United States Patent [19]

Aronson et al.

[11] Patent Number: 5,055,293
[45] Date of Patent: Oct. 8, 1991

[54] BIOLOGICAL PESTICIDE
[75] Inventors: Arthur I. Aronson; Peter E. Dunn, both of West Lafayette, Ind.
[73] Assignee: Purdue Research Foundation, West Lafayette, Ind.
[21] Appl. No.: 165,754
[22] Filed: Mar. 9, 1988
[51] Int. Cl.$^5$ ............................................. A61K 39/07
[52] U.S. Cl. ................................... 424/93; 435/252.5
[58] Field of Search ........................ 424/93; 435/252.5
[56] References Cited
FOREIGN PATENT DOCUMENTS
0238311 9/1987 European Pat. Off. .............. 424/93

OTHER PUBLICATIONS

"Insecticidal Activity of *Bacillus laterosporus*", Favret, M. E. and Yousten, A. A., Journal of Invertebrate Pathology, vol. 45, pp. 195–203 (1985).

Primary Examiner—Howard E. Schain
Assistant Examiner—Choon P. Koh
Attorney, Agent, or Firm—Barnes & Thornburg

[57] ABSTRACT

Corn rootworm infestations can be controlled by inoculating the soil with parasporal-inclusion forming species of *Bacillus laterosporus* to produce viable populations of that bacteria effective to reduce crop damage. Viable populations of *B. laterosporus* can be initiated by application to the soil, of effective amounts of vegetative cells or spores of the organism either in liquid supensions, or as coatings on seeds or granular substrates.

11 Claims, 1 Drawing Sheet

BIOLOGICAL PESTICIDE

This invention relates to a biological method for controlling field infestations of corn rootworm. More particularly this invention is directed to the use of viable populations of parasporal-inclusion-forming bacteria of the species *Bacillus laterosporus* to reduce crop damage caused by corn rootworm.

BACKGROUND AND SUMMARY OF THE INVENTION

Corn rootworms are the most serious pests of corn in the major corn growing regions of North America. Root feeding of the larvae has a pronounced effect on corn growth and corn yields. Corn rootworm infestations have been shown to decrease yields of corn by 13 to 16 bushels per acre. The present day toll paid by U.S. farmers in treatment costs and crop losses is estimated to be in the range of $1 billion per year.

Since crop rotation is the only practical, non-chemical control for corn rootworms [e.g., Western Corn Rootworm, *Diabrotica virgifera virgifera* (LeConte), and Northern Corn Rootworm, *D. barberi* (Smith and Lawrence)], there has been heavy reliance placed on the use of chemical insecticides. However the present day control of corn rootworms with soil insecticides has been complicated by additional technological problems. Not only has low levels of resistance developed to some of the newer insecticides, but accelerated microbial degradation has been noted where the soil microorganisms have developed a capacity to use the soil insecticide. Such has resulted in degradative rates of carbofuran and other soil pesticides as much as 10-fold higher in problem soils than in non-problem soils. These adverse factors, together with legal restrictions on use of insecticides because of potential user toxicity and environmental contamination, resulted between 1950 and 1983, in the withdrawal of recommendations for use of the following soil insecticides for corn rootworm control: benzene hexachloride, aldrin, dieldrin, heptachlor, chlordane, parathion, diazinon, disulfoton, fensulfothion, isofenphos, carbaryl, metalkamate, landrin, and carbofuran. Only a few new insecticides have been introduced during the 1980's as replacements. Thus the prognosis for long-term continuation of successful soil insecticide control of rootworms does not look promising.

There are a number of parasporal-body-forming Bacilli that produce toxins for insect larvae. A number of soil bacteria effective in the control of insects of several orders have been commercially available since the 1960's. Examples are *Bacillus popilliae* for the control of Japanese beetle (Scarabaridae), several serotypes of *Bacillus thuringiensis* for the control of Lepidoptera pests of food and fiber crops and *B. thuringiensis* subsp. israelensis effective on Diptera, i.e., mosquitoes and black flies. A more recent isolate, *B. thuringiensis* subsp. tenebrionis, seems to be toxic to certain Coleoptera, that is, the Colorado potato beetle. In all cases, perhaps with the exception of *B. popilliae*, the bacteria produce a proteinaceous parasporal inclusion during sporulation. Generally, it is this inclusion which contains the lethal agent; that is, it is composed of protoxin molecules which are cleaved in the larval gut to toxins. In a few cases, the bacterial spore may also participate in the killing, and in the case of *B. popilliae* (and a few less prevalent related organisms), it is probably the multiplication of the bacterium in the larval haemolymph that results in the death of the host.

There has been no isolation/description of soil bacteria that are effective on the coleopteran species, Diabrotica (corn rootworm).

In view of the above-mentioned technological limitations on chemical control of corn rootworm, including Pest resistance, non-biodegradability, and animal toxicity, a biological control agent for corn rootworm would be a most desirable alternative. Accordingly, this invention is directed to the use of parasporal-inclusion-forming *Bacillus laterosporus*, which when present in the soil of growing corn crops are effective for controlling corn rootworm infestations. Compositions comprising (1) viable parasporal-inclusion-producing bacteria of the species *Bacillus laterosporus* in the form of vegetative cells or spores, and (2) an agriculturally acceptable carrier therefor can be applied to the soil in conjunction with (either before, with or after) planting of a corn crop.

DETAILED DESCRIPTION OF THE INVENTION

Figure 1:
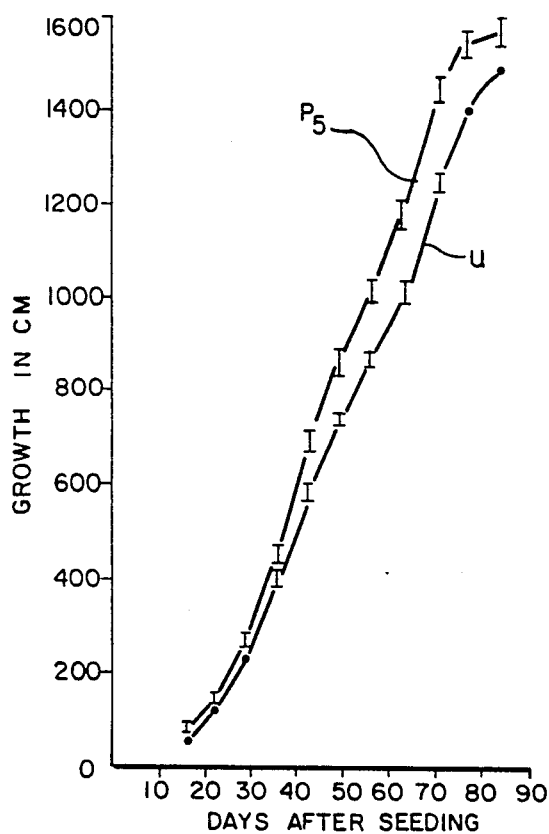
FIG. 1 is a graphical illustration of the protection afforded growing corn from *Diabrotica virgifera virgifera* (Western Corn Rootworm) by *Bacillus laterosporus* P5 (ATCC 53694).

Soil samples were screened for bacteria capable of controlling corn rootworms. Soil samples were obtained from cornfields which had not been treated with insecticides in recent years. They were taken from fields infected with corn rootworm and from fields apparently free of corn rootworm infestation. Portions of soil (100 mg) were suspended in buffer, heated and plated on enriched media. The plates were incubated for sufficient time to permit cells to sporulate and these were then screened in the phase microscope for unusual morphology and particularly the presence of parasporal inclusions. The screening procedure turned up several unique isolates, all with similar morphology but present only in soil samples from non-infested portions of one field located at the Throckmorton Purdue Agricultural Center in Randolph Township, Tippecanoe County, Ind. One particular isolate, designated as *Bacillus laterosporus* P5, was found in a low frequency in eight of nine samples from non-infested soil but was absent in all nine samples of soil from areas known to be infected with corn rootworms. This correlation prompted initial tests of the toxicity of the *B. laterosporus* P5 species (cells or spores thereof) on various Lepidoptera as well as on corn rootworm. No toxicity was observed on the larvae of three test Lepidoptera (*Manduca sexta, Trichoplusia ni, Heliothis virescens*) but experiments with the Western Corn Rootworm looked promising.

The Bacillus isolate, designated *Bacillus laterosporus*, P5 was deposited on Nov. 23, 1987, at the American Type Culture Collection and was assigned ATCC Designation "53694". Other isolates of *Bacillus laterosporus* having either free or attached parasporal inclusions have been found in soil samples free of corn rootworm.

Both vegetative cells and spore suspensions were tested on corn seedlings in flats supplemented with larvae of Western Corn Rootworm. The mean height of the plants was then measured for at least 35 days. Those plants growing in flats infested with corn rootworm grew slowly for about 14 days and then stopped while plants exposed to both rootworm and either cells or spores of one of the *B. laterosporus* isolates continued growing at the control rate for 18-20 days before tapering off. Other studies confirming the efficacy of parasporal-inclusion-forming *Bacillus laterosporus* species for control of corn rootworm have been conducted and are described below.

The plant protection properties of the P5 strain of *Bacillus laterosporus* were evaluated in a greenhouse study using Ohio 43 inbred corn planted in 15 cm diameter plastic pots. Individual kernels were planted approximately 2.5 cm deep in Promix, a commercial planting medium, that had been water saturated prior to being placed in the pots. There were two groups of treatments, and initially 13-14 pots were planted for each treatment. The first group was designed to evaluate the effects of actively growing *B. laterosporus* cells and the second group to evaluate *B. laterosporus* spores. Cells were applied with NYSM growth medium while spores were applied with water. There were three treatments in each group. In the first group, the treatments were: 1) and 2), 15 ml of sterile medium per pot and 3) 15 ml of NYSM media containing approximately $3.0 \times 10^8$ cells/ml. In the second group, treatments were: 4) 15 ml $H_2O$ containing approximately $6.0 \times 10^8$ spores/ml, and 5) and 6), 15 ml sterile $H_2O$. Treatments were to the surface and applied above the kernel at planting time. Eight days after Planting, germination was evident. The number of Pots with germinated corn was reduced to 10 per treatment, and treatments were repeated. The following day, each plant in treatments 2, 3, 4 and 5 was infested with Western Corn Rootworm, *Diabrotica virgifera virgifera* (LeConte), eggs by placing 0.5 by 2.0 cm filter paper strips bearing the eggs 2.5 cm deep at the base of each plant. Treatments 1 and 6 were not infested. To estimate hatch time and rate, 20 eggs were kept on moist filter paper in a petri dish. (Beginning five days after infestation, 85% of these hatched over a three day period.) Extended plant height was the criterion used to evaluate treatment effect. Heights 48 days after planting were determined for each treatment and treatment means were compared using the general linear model (GLM) procedure on the Statistical Analysis System (SAS).

In the spore group, results indicate that plant protection occurred in response to treatment of the planting medium with *B. laterosporus*. Infested plants treated with spores were numerically taller than those without spores (74.4 vs. 63.3 cm) but the difference was not statistically significant at the 95% confidence level. Uninfested plants (98.6 cm) were significantly taller than either of the infested treatments.

In the cell group, however, no protection was evident because plants treated with the *B. laterosporus* cells were the shortest among the three treatments. Uninfested plants were significantly (probability <0.05) taller than infested plants treated with cells (100.6 vs. 80.4 cm) but not significantly taller than infested plants treated with cell free medium (92.9 cm). There was no significant difference in mean height between the infested groups.

FIELD APPLICATION

Large scale preparation of vegetative cells or spores of *B. laterosporus* can be accomplished in any of a variety of art-recognized complex media containing Yeast extract and peptones. Two liter flasks containing up to 500 ml of media can be inoculated and incubated in a rotary shaker at 30°-37° C. for 12-14 hours to provide the inoculum. Fermentor flasks containing the same medium can then be used for the growth of 10-80 l. Growth times will vary depending upon the nutrient medium, temperature, aeration and growth stage desired. Under typical cell growth conditions vegetative cells can be harvested after 8-10 hours; spores (plus inclusions) are harvested after 24-36 hours. Harvesting may be done in a Sharples continuous flow centrifuge. The resulting cell paste can then be suspended to any desired final concentration (determine the cell numbers with a Petroff-Hauser counter) in either a nutrient-containing medium, distilled water or a buffer of choice. The spores will keep well, but vegetative cells should be prepared immediately before field application.

Field application of *B. laterosporus* in accordance with this invention can thus be accomplished as a cell or spore suspension in an agriculturally acceptable liquid carrier or as a granular formulation in which viable cells or spores are sprayed or otherwise coated onto a granular substrate. The substrate can be formed, for example, from an inert clay or other agriculturally acceptable mineral or organic material. Granular materials typically range in size from 20 to 80 mesh, sized for easy handling, for example, in equipment designed for application of granular fertilizers. The granular substrate is sprayed with a solution of viable cells and/or spores, optionally containing cell nutrients and coating-excipients, and then dried. Alternatively, the Bacillus species (cells or spores) can be applied, for example, with a nutrient supplement or binder as a seed treatment so that a viable rootworm-confronting population of the microorganism is initiated in the soil environment of the planted seed.

Currently, granular formulations of commercially available rootworm insecticides are applied in an 18 cm band or in furrow at planting time. This method has also been tested on other biological insecticides such as *Beauveria bassiana*. Granular formulations of *B. laterosporus* spores can be applied in a similar manner at planting time in equipment already present on corn planters. Spores could also be suspended in water and applied as a spray at planting time. Again, the required equipment is currently used by farmers in other applications. Results from small plot field studies can be evaluated to determine optimal rates and methods of applications. Since planting densities are preset, initial application rates in terms of active ingredient per acre can be determined by extrapolation of the greenhouse treatment levels.

FIELD TESTS WITH *B. LATEROSPORUS* VARIANT P5 VERSUS WESTERN CORN ROOTWORM (*DIABROTICA VERGIFERA VERGIFERA*)

In this test, 12 plots were laid out on part of a ⅓ acre field. Each plot contained 4 rows 463 cm long and 84 cm apart and were spaced 168 cm from neighboring plots. All plots were seeded with OHIO 43 corn on May 26. Diabrotica eggs taken from 2-4° C. storage in soil were spread on filter paper strips (20 eggs/strip) on May 22 and incubated at room temperature with high humidity in the dark for hatching (60-80%) some 14 days later at which time most corn shoots were showing. Controls consisted of one plot with corn only, two with corn and rootworms and one corn rootworm treated with Cyanamid's Counter ® brand insecticide (15 gm/row). Other plots were treated (30-40 minutes) Prior to the addition of the about-to-hatch egg papers with both sporulated and vegetative cultures of the test strain and with control cultures of *B. laterosporus* not containing inclusions (NRS-590 in Table I). Concentration of cells or spores varied from $2\times10^7$ to $1\times10^{11}$ per meter of row. Cells or spores grown up in 15 liter batches of NYSM broth, harvested by a "Pellicon" apparatus (Millipore), pelleted by centrifugation and resuspended in water (spores) or NYSM (cells) to 150 mls. The test suspensions at the calculated concentrations were suspended to 1 liter (water for spores and NYSM media for vegetative cells) and sprayed down the rows using a Green-Cross "Superspray" hand pump bottle. A one liter water spray followed to "wash in" the culture. Egg Papers were placed 1-2 cm from the developing roots. Corn growth (plant height) was measured each week for 12 weeks and on October 20 the cobs were weighed for yield.

TABLE I

MEAN Plant Height (and Std. Error) in Cm
(Cultures added with rootworms to soil)
Doses given per row (463 cm)
20 rootworms/plant
4 row/plot, n = 36–40

| | PLOT # | | | | | | |
|---|---|---|---|---|---|---|---|
| | 9 | 1 | 2 | 3 | 4 | 5 | 6 |
| Day of Growth | COUNTER CONTROL | CONTROL (No Added Rootworms) | A7 ($10^{10}$) Veg. | P5 veg ($10^{10}$) | Rootworm Only Control | ($10^{10}$) P5 Spores | NRS - 590 ($10^{10}$) |
| 16 | 59.9 | 78 | 71.6 | 82.3 | 77.1 | 53.9 | 40.6 |
| | (3.1) | (4) | (55) | (5.2) | (4.2) | (3.4) | (3.4) |
| 22 | 154.6 | 169 | 131.7 | 152.7 | 143 | 117.7 | 95.9 |
| | (5.1) | (7) | (8.3) | (8.1) | (5.2) | (5.8) | (5.1) |
| | 281 | 309 | 252 | 273 | 234 | 182.5 | 178.5 |
| | (17) | (14) | (15) | (16) | (13) | (14) | (9) |
| 36 | 508.7 | 533 | 443 | 467 | 414 | 335 | 318 |
| | (24) | (20) | (21) | (23.6) | (19.7) | (22) | (16.2) |
| 43 | 756.6 | 749 | 638 | 701 | 618 | 479 | 515 |
| | (17) | (14) | (18) | (20.1) | (20) | (36) | (17.2) |
| 50 | 900 | 902 | 781 | 875 | 827 | 716 | 715 |
| | (30) | (23) | (24) | (28.6) | (23) | (31) | (19.3) |
| 57 | 1032 | 992 | 916 | 1038 | 983 | 856 | 850 |
| | (19) | (36) | (29) | (29.4) | (23) | (33) | (29) |
| 64 | 1159 | 1074 | 1088 | 1183 | 1160 | 958 | 1042 |
| | (25) | (49) | (32) | (39) | (25) | (49) | (21.5) |
| 72 | 1401 | 1287 | 1384 | 1460 | 1427 | 1225 | 1313 |
| | (40) | (52) | (34) | (27) | (23) | (44) | (26.1) |
| 78 | 1508 | 1467 | 1512 | 1561 | 1560 | 1390 | 1490 |
| | (37) | (36) | (29) | (23) | (17) | (42) | (20.9) |
| 85 | 1554 | 1495 | 1569 | 1573 | 1603 | 1535 | 1620 |
| | (17) | (32) | (22) | (35) | (12) | (31.1) | (15) |
| CORN YIELD | 151 | 136 | 140 | 155 | 94 | 127 | 144 |

| | PLOT # | | | | |
|---|---|---|---|---|---|
| | 7 | 8 | 10 | 11 | 12 |
| Day Of Growth | P5 Spores + Inc ($5\times10^{10}$) | Rootworm Only Control | ($10^8$) P5 Spores | ($10^{10}$) P5 2b | ($10^{10}$) A7 Spores |
| 16 | 64 | 55.7 | 48.3 | 73.9 | 52.5 |
| | (3.8) | (2.4) | (5.3) | (6.3) | (5.5) |
| 22 | 130 | 125.3 | 115.7 | 143.9 | 110 |
| | (6.3) | (4.1) | (8.7) | (11.2) | (7.8) |
| | 249 | 243 | 213 | 287.6 | 205 |
| | (11.7) | (8.5) | (18) | (19.5) | (12.1) |
| 36 | 446 | 457 | 360 | 438 | 326 |
| | (16.8) | (11.7) | (37) | (31.4) | (19.6) |
| 43 | 647 | 675 | 646 | 655 | 421.4 |
| | (17.4) | (23) | (20) | (34) | (33) |
| 50 | 838 | 816 | 807 | 818 | 577 |
| | (18) | (24) | (25) | (41) | (28) |
| 57 | 969 | 951 | 960 | 959 | 671 |
| | (21) | (15) | (26) | (39) | (29.3) |
| 64 | 1137 | 1075 | 1114 | 1076 | 781 |
| | (29) | (16.8) | (30.5) | (53) | (27) |
| 72 | 1419 | 1308 | 1369 | 1296 | 954 |
| | (29.5) | (24.9) | (36.3) | (39) | (36) |
| 78 | 1549 | 1479 | 1484 | 1406 | 1125 |
| | (21) | (19.3) | (29) | (33) | (44) |
| 85 | 1587 | 1524 | 1487' | 1462 | 1326 |
| | (19) | (13) | (53). | (29) | (37) |
| CORN YEILD | 146 | 133 | 132 | 140 | 114 |

Raw data for 11 weeks of this 12 plot test are reported in Table I. The best control growth performance was shown by both the corn without added rootworms and the "Counter" treated plots; the latter out-performing the former in later growth and corn yield. A group of plots (Plots 2, 4, 8 and 12) unprotected by Counter or by the test culture or treated with a culture of *B. laterosporus* not containing inclusions (NRS-590) were suppressed in growth an average of 14% over the 12 weeks and were 20-22% behind Counter control from day 22 to day 42. Corn yields of these unprotected, rootworm treated plants were suppressed by 20%. Addition of resting spores+inclusions of the P5 culture at a dose $2 \times 10^7$/meter showed no improvement, at $10^{10}$ only slight protection and at $10^{11}$ possibly moderate protection. The vegetative culture of P5, however, added at $10^{10}$/per row ($2 \times 10^9$/m) showed full protection of growth and a 29% improvement of corn yield over the unprotected controls (FIG. 1 and Table II). Lower doses of vegetative cells were not tested.

Because of a suspected endogenous infestation of *Diabrotica virgifera* in the test field, a second series of tests was set up later in the summer when such eggs were presumably hatched out. In this study because of the apparent early failure of P5 spores and inclusions to show Protection, it was decided to pretreat the soil with test cultures. These were sprayed down the rows as in the previous study on Jul. 9.

TABLE II

| MEAN CORN YIELD Grams/Plant | |
|---|---|
| Control Plot (Plot #1) | 136 |
| Counter ® Plot (Plot #9) | 151 |
| 2 Rootworms Only Plots (Plots #4 and 8) | 113 |
| 4 Unprotected Plots (Plots 2, 4, 8 and 12) | 120 |
| P5 Vegetative Cell Plot (Plot #3) | 155 |

On Jul. 16, the rows were seeded and on Jul. 21 a moist paper strip with 20-30 eggs was added. The positive control here was not treated with insecticide and given no worms. Plant height was measured as before but the study was terminated at 60 days.

The data for these eight plots is reported in Table III. The week's pretreatment apparently made the P5 spores as effective as the vegetative cells.

Figure 2:
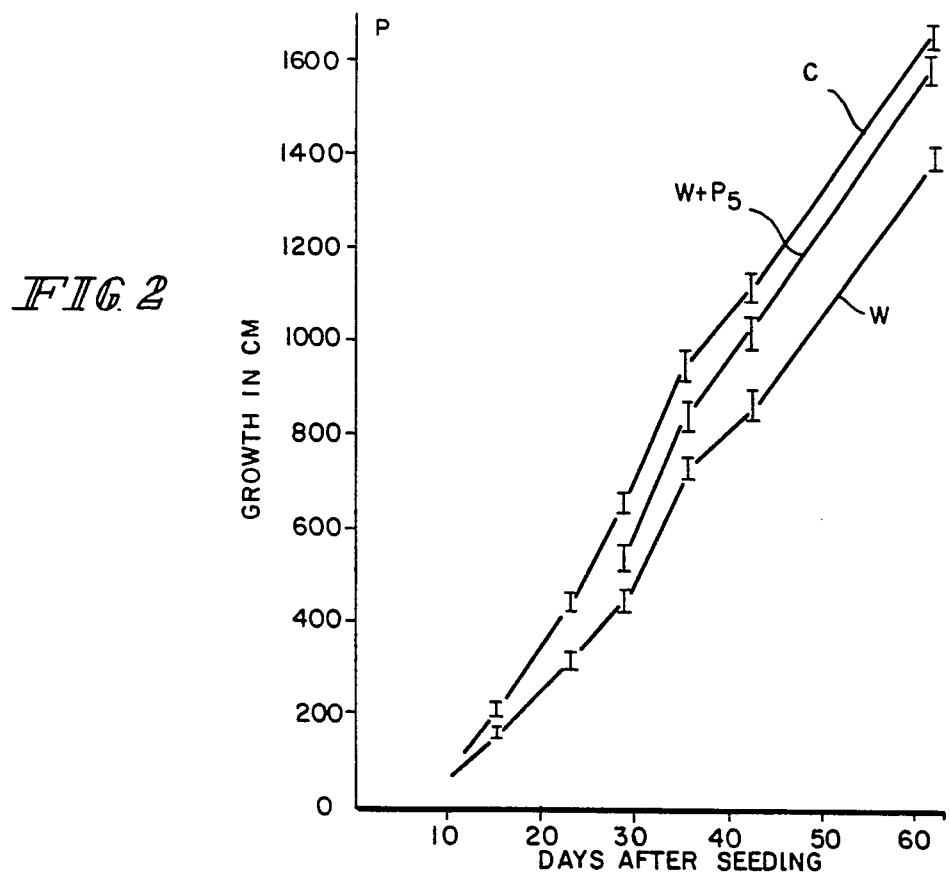
FIG. 2 is a graphical illustration similar to that in FIG. 1 except showing protection by treatment with *B. laterosporus* P5 spores and inclusions.

A graph of controls without rootworms (C) and with rootworms (W) are compared to the rootworms plus P5 spore-treated plot (W+P5) in FIG. 2. Together these field tests suggest that vegetative cells are the active form rendering protection of corn plants to *Diabrotica virgifera* damage. Given time to germinate, the spores also become effective.

Separate laboratory tests indicated no immediate toxicity when larvae (1st, 2nd and 3rd instar) were exposed to spores plus inclusions or purified inclusions of P5. Late additions of culture to infested corn were not protective. The apparent protective effect of P5 in growth studies suggests the culture, in vegetative form, either invades the very young larvae for immediate or later damage or that it blocks the receipt or response of the rootworm to the corn root signal that directs it to the roots.

TABLE III

Mean Plant Height (and Std. Error) in Cm
Cultures added 7 days before Planting
(July 9, 1987)
n = 26-28
doses in #/row (1080 cm)
20 rootworms/plant

| Day of Corn Growth (Since Planting) | Plot 13 Control Corn Only | Plot 14 Rootworms Only Control | Plot 15 P5 Spores + Inc. $10^{10}$ | Plot 16 A7 Spores | Plot 17 P5 Spores + Inc. $10^9$ | Plot 18 P5 Cells $10^{10}$ | Plot 19 Rootworms Only Control | Plot 20 Mut. P5 21 Inclusions + Some Sp. $10^{10}$ |
|---|---|---|---|---|---|---|---|---|
| 15 | 222 (8.5) | 181 (8.7) | 217 (6.1) | 184 (10) | 189 (8.4) | 203 (9.6) | 164 (8.9) | 178 (9.9) |
| 23 | 465 (16) | 399 (13) | 447 (13) | 408 (14) | 380 (26) | 417 (16) | 332 (19) | 345 (24) |
| 29 | 660 (20) | 578 (17) | 634 (17) | 575 (17) | 502 (42) | 556 (29) | 466 (27) | 521 (23) |
| 36 | 959 (22) | 861 (21) | 952 (21) | 879 (20) | 853 (29) | 854 (32) | 756 (33) | 755 (34) |
| 43 | 1134 (21) | 1041 (28) | 1127 (21) | 1096 (41) | 1023 (31) | 1035 (31) | 884 (52) | 899 (37) |
| 63 | 1682 (20) | 1611 (26) | 1635 (24) | 1589 (26) | 1573 (30) | 1616 (34) | 1442 (48) | 1415 (60) |

We claim:

1. A method for reducing corn crop damage caused by corn root worm infestation, which method comprises treating the soil used for growing said crop to initiate growth of an effective population of a parasporal-inclusion-forming bacterium *Bacillus laterosporus* in said soil.

2. The method of claim 1 wherein the viable bacterial population in the soil is initiated by application to the soil of a composition comprising vegetative cells or spores of said bacteria.

3. The method of claim 2 wherein said composition is applied to the soil as a seed coating.

4. The method of claim 2 wherein said composition is applied as a bacterial cell or bacterial spore suspension in an aqueous medium.

5. The method of claim 2 wherein the composition is applied to the soil at the time of crop planting.

6. The method of claim 2 wherein the composition is applied to the soil in advance of crop planting.

7. The method of claim 1 wherein the Bacillus species is *Bacillus laterosporus* P5 ATCC 53694.

8. A composition of matter for control of corn root worm infestations, said composition comprising the parasporal-inclusion-producing bacteria *Bacillus laterosporus* P5 ATCC 53694 in the form of vegetative cells or spores and an agriculturally acceptable carrier therefor.

9. The composition of claim 8 wherein the carrier is an aqueous medium.

10. The composition of claim 8 wherein the carrier is a granular substrate.

11. The composition of claim 8 wherein the carrier is seed corn.

* * * * *